United States Patent [19]

DeVries et al.

[11] Patent Number: 5,041,084
[45] Date of Patent: Aug. 20, 1991

[54] SINGLE STAGE VENOUS CATHETER

[75] Inventors: James H. DeVries; Kenneth R. Jonkman, both of Grand Rapids, Mich.

[73] Assignee: DLP, Inc., Grand Rapids, Mich.

[21] Appl. No.: 564,606

[22] Filed: Aug. 9, 1990

[51] Int. Cl.⁵ .............................................. A61M 3/00
[52] U.S. Cl. ...................................... 604/43; 604/169; 604/264; 604/280
[58] Field of Search ............. 604/264, 249, 256, 280, 604/281, 282, 283, 43, 4, 27, 169, 170

[56] References Cited

U.S. PATENT DOCUMENTS

| | | | |
|---|---|---|---|
| 3,630,207 | 12/1971 | Kahn et al. | 604/282 |
| 4,129,129 | 12/1978 | Amrine | 604/43 |
| 4,596,548 | 6/1986 | DeVries et al. | 604/4 |
| 4,787,882 | 11/1988 | Claren | 604/4 |
| 4,863,441 | 9/1989 | Lindsay et al. | 604/264 X |

*Primary Examiner*—John D. Yasko
*Attorney, Agent, or Firm*—Barnes, Kisselle, Raisch, Choate, Whittemore & Hulbert

[57] ABSTRACT

A single stage catheter which is used in open heart surgery to by-pass blood from the heart to a life support machine. The single stage catheter has a spiral lead flute for insertion into the inferior vena cava of the heart and a root section with multiple openings to be positioned in the right atrium of the heart. The flutes of the spiral lead to small quadrant openings in the end of the root section which also has long and short axial slot openings leading to the interior of the catheter. An obturator is designed to block the long and short axial slots during insertion to allow flow only through the quadrant openings to the interior of the obturator.

9 Claims, 3 Drawing Sheets

SINGLE STAGE VENOUS CATHETER

FIELD OF INVENTION

Catheters introduced into the heart organ in the course of open heart surgery to divert blood to a life support machine.

BACKGROUND AND OBJECTS OF THE INVENTION

In heart surgery, life support machines are utilized to perform temporarily the function of the heart and lungs while the patient's heart is being surgically serviced such as the repair of heart wall lesions, installation of a valve, and by-pass artery work. The life support machine must take the flowing blood from the patient, maintain the temperature, pressure, and flow rate within certain physiologic limits, and provide the lung function.

In the course of an operation of this type, it is essential that a change-over be accomplished from the natural heart function to the machine. This involves installation of a venous return catheter into the right atrium (chamber) of the heart to serve as a drainage supply connection to the pumping machine. Experience has shown that, when used in certain procedures such as coronary artery by-pass to the circumflex coronary artery, anatomical variations and intra-operative manipulation of the heart may cause a reduction in venous drainage due to distortion of the atrial walls and vena cava or shifting of the catheter position.

The traditional method of venous drainage has been to place two catheters, one into the superior vena cava, and the other one into the inferior vena cava. This method provides good venous return in all operative circumstances but requires that additional time be spent placing the two catheters. Single catheter venous drainage from the right atrium was developed to simplify and shorten the time required for catheterization. However, the disadvantage of single catheter drainage from the right atrium only is its limitation to those procedures not requiring the previously discussed operative manipulations which reduce the blood flow. A two-stage catheter has also been developed to combine the desirable simplicity, convenience, and time savings of the single catheter with the higher reliability of the two catheter technique.

It is an object of the present invention to provide a single stage venous catheter which achieves the advantages of the double catheter on the two-stage catheter, which is easily installed and which insures adequate drainage during a heart operation. It is a further object to provide a catheter designed for maximum flow and one which can be installed with a minimal loss of blood and through a single aperture created by the amputation or incision of a portion of the distal appendage.

One type of two-stage catheter is disclosed in Bruce A. Amrine U.S. Pat. No. 4,129,129, issued on Dec. 12, 1978.

The present invention relates to a single stage venous catheter which is an improvement over the single-stage catheter disclosed in the DeVries amd Williams U.S. Pat. No. 4,596,548, issued Jan. 24, 1986, and assigned to the assignee of the present application.

It is a further object to provide a single stage catheter which has an improved tip configuration interlocked with the basket of the catheter. An array of full length and short slots in the basket increase the flow area while permitting an obturator to block both slot lengths for introduction of the catheter into the heart cavity, and to prevent loss of blood through the slots during insertion.

Other objects and features of the invention will be apparent in the following detailed description and claims in which there is set forth the invention together with details to enable a person to practice the invention, all in connection with the best mode presently contemplated for the invention.

BRIEF DESCRIPTION OF THE DRAWINGS

DRAWINGS accompany the disclosure and the various views thereof may be briefly described as.

BRIEF DESCRIPTION OF THE INVENTION

The invention is directed to a single stage catheter which is used in open heart surgery to by-pass blood from the heart to a life support machine. The single stage catheter has a spiral lead flute for insertion into the inferior vena cava of the heart which acts as a stent to keep the vena cava patent and a root section with multiple openings to be positioned in the right atrium of the heart. The flutes of the spiral lead to small quadrant openings in the end of the root section which also has long and short axial slot openings leading to the interior of the catheter. An obturator is designed to block the long and short axial slots during insertion to prevent blood loss and to allow flow only through the quadrant openings to the interior of the obturator.

DETAILED DESCRIPTION OF THE INVENTION AND THE MANNER AND PROCESS OF USING IT

Figure 1:
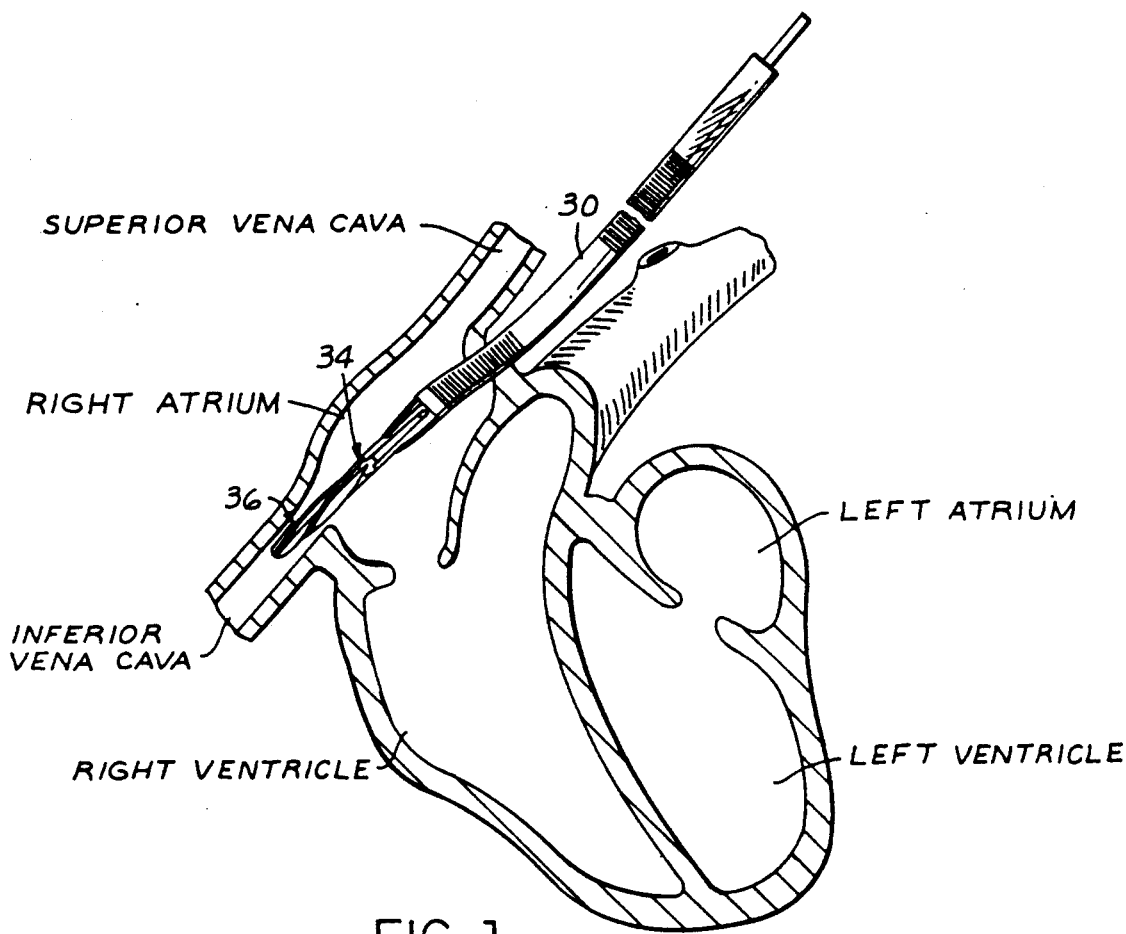
FIG. 1, a sectional view of a heart illustrating the operative position of a single stage catheter.

In FIG. 1, a diagrammatic section of a human heart is illustrated showing the superior vena cava, the right atrium and the inferior vena cava above the right ventricle chamber. The single stage catheter shown in FIG. 1 comprises a flexible, coil-reinforced tube 30 with a root reducer body 32, a tip end 34 and a flexible, spiraled feeder end 36. The body 32 has a reduced end which is secured to the distal end of the tube 30 at 38.

Figure 9:
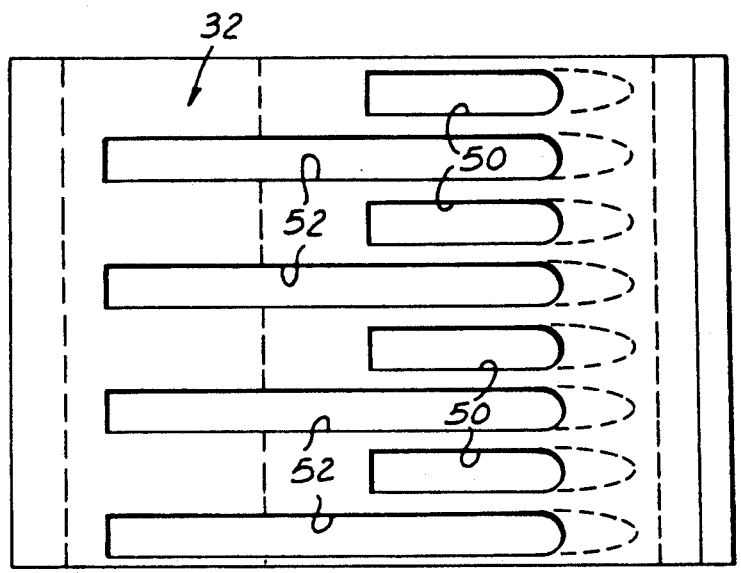
FIG. 9, a development of the catheter basket to illustrate the slots.

FIGS. 2 to 5 show these parts in greater detail. The reducer body 32 tapers down gradually at 40 and more sharply at 42 to a cylindrical section 44. There are axially extending slots in the root reducer body 32, some short as at 50 which are in the section 40 and some long as at 52 which extend distally from the section 40 down through the section 44. The tip end 34 is rounded at the distal end 54 and has short projections 56 which insert into the distal end of the long slots 52 and are secured by sonic welding, solvent bonding, or a suitable cement. The tip 34 has an open distal wall 58 which is divided into four quadrant openings 60 (FIG. 3) by the four fins of the feeder end 36 so that the quadrant openings 60 register with section flutes 62 on the spiraled feeder end. In FIG. 9, a layout development of the reducer body 32 is illustrated showing the short slots 50 and the long slots 52.

The body 32 has a thin collar 70 at the distal end which inserts into the tip end 34 and to which the tip end is secured. The proximal end of the body 32 also has an extending collar 72 which inserts into the end of the tube 30 and is sonic welded or otherwise bonded to the tube.

Figure 2:
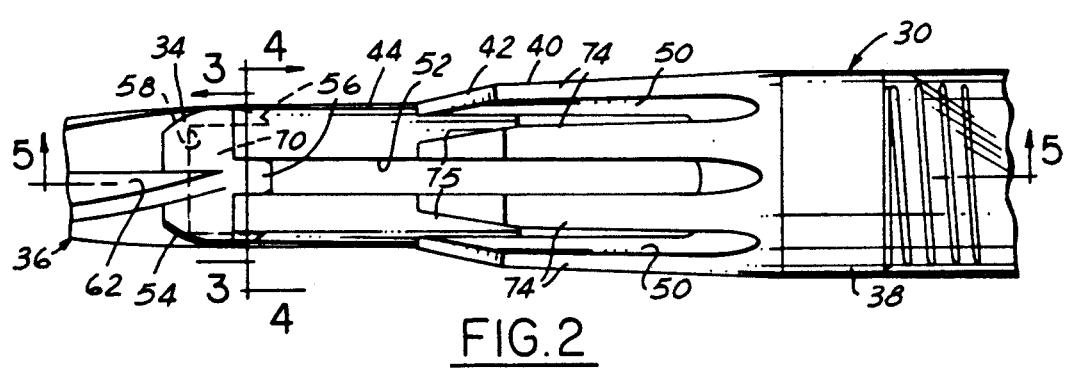
FIG. 2, an elevation of the main element of the catheter.
Figure 3:
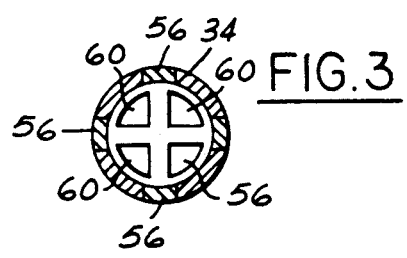
FIG. 3, a cross-section on line 3—3 of FIG. 2.
Figure 4:
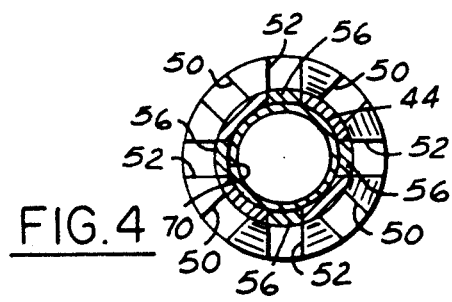
FIG. 4, a cross-section on line 4—4 of FIG. 2.
Figure 6:
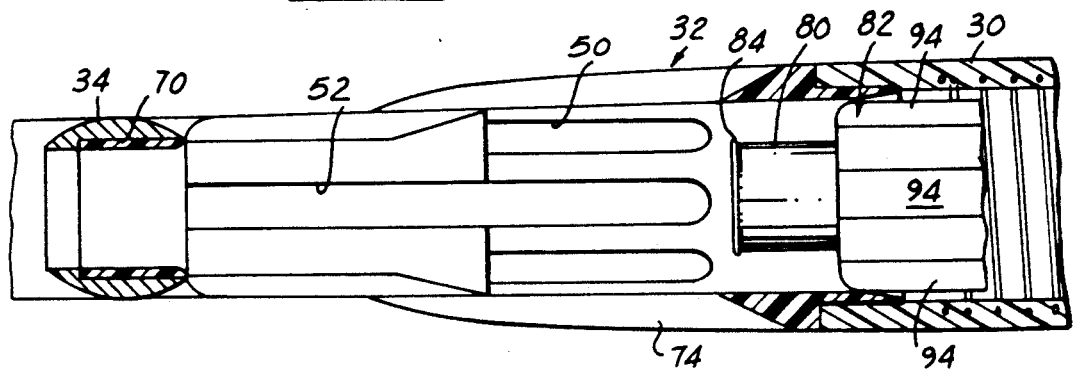
FIG. 6, a longitudinal section of the open catheter with the occluder withdrawn.
Figure 7:
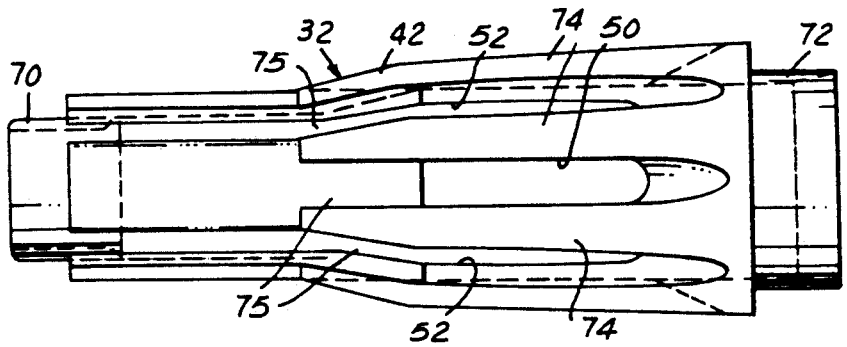
FIG. 7, a view of the main body of the catheter basket with the tip and tube removed.

In FIG. 7, the body 32 is turned 90° from the elevation shown in FIG. 2 and FIG. 6 to illustrate the short slots 50 and the long slots 52 as well as the end collars 70 and 72. As shown in the drawings, on each side of the short slots 50 in the tapering area 40 of the cage body 32 are ribs 74 (FIGS. 2 and 7) which taper down and overlie the smaller distal end of the cage, thus providing smooth axial passages 75 into the short slots 50. Thus, even with flesh contact on the side of the catheter cage blood can flow into the slots.

In the use of a venous catheter it is difficult to insert into the wall of the heart in an area adjacent the superior vena cava without blood loss through the openings in the body 32. It is, therefore, desirable to utilize an obturator tube inserted into the catheter to occlude the openings during insertion.

Figure 5:
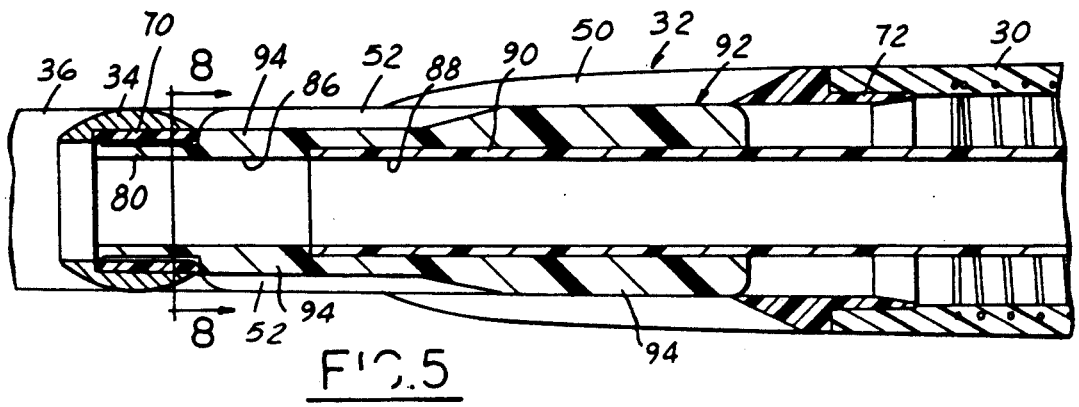
FIG. 5, a longitudinal section of the catheter taken on line 5—5 of FIG. 2 with an occluder in place.

In FIG. 6, the distal end 80 of an obturator 82 is shown partially projected into the body 32. In FIG. 5, the obturator is fully inserted into the body 32. The obturator has a distal end 80 which is received in the collar 70 and a small lip 84 provides a seal within the collar so blood flowing along the grooves 62 of the spiral flow guide 36 into the right atrium can enter only the central opening 86 of the obturator and then the passage 88 within the obturator tube 90.

Figure 8:
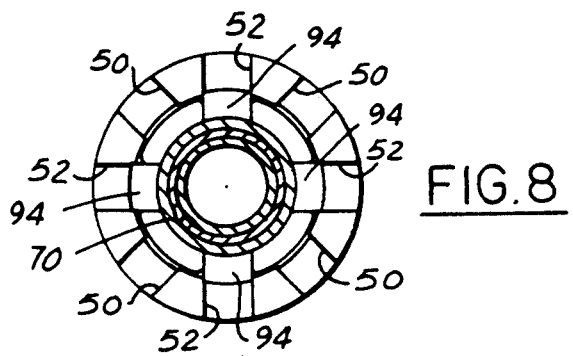
FIG. 8, a sectional view of the catheter on line 8—8 as illustrated in FIG. 5.

In addition, the head end of the obturator has a cylindrical proximal portion 92 which closes the interior of the body 32 and especially the short slots 50 and the proximal ends of the long slots 52. Between the portion 92 and the distal end 80 are four ribs 94 on the obturator which close the distal ends of the long slots 52. In FIG. 8, a sectional view on line 8—8 of FIG. 5 illustrates the obturator in place in the catheter body 32.

Thus, when the venous catheter is introduced into the right atrium after a suitable incision in the heart wall, with the obturator in place, the only flash back of blood through the quadrant openings 60 is contained by the tube 90 of the obturator. Once the catheter body 32 is fully received in the right atrium of the heart with the spiral flexible flow guide 36 in the inferior vena cava, the obturator may be removed and the venous catheter is ready to function in connection with extracorporeal equipment.

Figure 10:
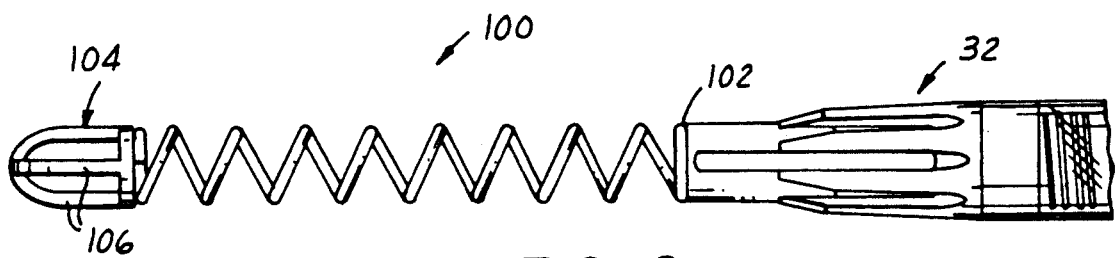
FIG. 10, an elevation of an alternate catheter tip.

It should be emphasized that the spiral tip end 36 has as its main purpose the projection into the inferior vena cava to serve as a stent to prevent occlusion of the cava when the heart is manipulated. The blood entering the catheter is all collected from the right atrium. In FIG. 10, a modified stent protection 100 is illustrated in the form of a thermoplastic or stainless steel wire coil secured to the distal end of the catheter at 102 and having a round-nosed pilot tip 104 at the distal end of the coil with spacer fins 106.

Figure 11:
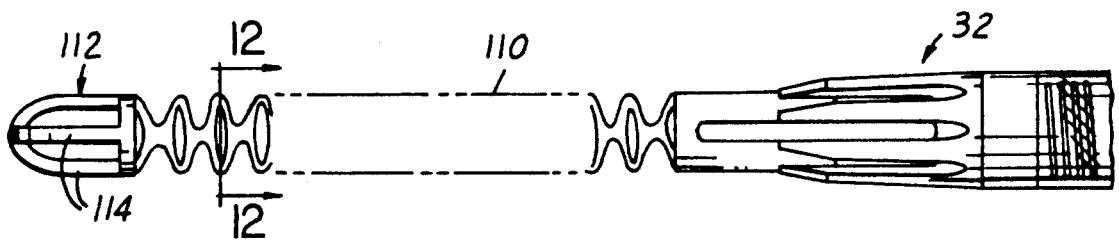
FIG. 11, an elevation of a second alternate catheter tip.
Figure 12:
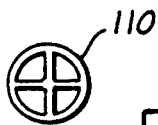
FIG. 12, a sectional view on line 12—12 of FIG. 11.

In FIG. 11, a modified stent 110 is shown formed of thermoplastic material molded in the form of a net which allows free longitudinal flow. A round-nosed pilot tip 112 having spaced fins 114 again provides free flow from the inferior vena cava to the right atrium and serves to prevent collapse and blockage of the inferior vena cava. The section of the modified stent 110 shown in FIG. 12 illustrates that the net formation allows free flow through the stent while it prevents collapse of the inferior vena cava.

What is claimed is:

1. A single stage venous return catheter for insertion into the right atrium of the heart to carry blood of the patient to an extracorporeal life support machine which comprises:
   (a) a main hollow cage body having a distal end and a proximal end, a plurality of wall slots in said body open to the interior thereof and extending axially of said body,
   (b) a tubular connector joined with the proximal end of said body having a passage open to the interior of the body,
   (c) a rounded tip secured to the distal end of said body having an open distal end, and
   (d) an inferior vena cava stent affixed to the distal end of said tip projectible into the cava to prevent collapse of the cava during heart manipulation and having passages to allow flow through the stent to the right atrium of the heart,
   (e) said slots in said cage body comprise a plurality of long slots spaced circumferentially around said body extending substantially the length of said body and a plurality of short slots interspersed with said long slots extending at the proximal end of said body about half the length of said body.

2. A single stage venous return catheter as defined in claim 1 in which said cage body has a large base diameter at a proximal end adjoined to said tubular connector and a reduced diameter at the distal end joined to said tip, said long slots being circumferentially spaced around said body extending substantially the length of said body and said short slots circumferentially interspersed with said long slots being disposed in the large base diameter at the proximal end of said cage body.

3. A single stage venous return catheter as defined in claim 2 in which ribs in said large diameter are disposed on each side of said slots and extend in spaced radial relation to said smaller diameter to provide flow passages into said slots.

4. A single stage venous return catheter as defined in claim 1 in which said stent comprises a spiraled, flexible, finned and fluted feeder end secured to said tip, the fins of said feeder end dividing said open tip end into sector openings, each registering with a flute in said feeder end.

5. A single stage venous return catheter as defined in claim 1 in which said stent comprises an elongate open coil having a pilot tip.

6. A single stage venous return catheter as defined in claim 1 in which said stent comprises an elongate body in the form of a molded net construction having open passages for longitudinal flow.

7. A single stage venous return catheter as defined in claim 1 in which the distal end of said body is divided into circumferentially spaced ribs between said long slots, and said tip has circumferentially spaced notches to receive and be secured to the distal end of said spaced ribs.

8. A single stage venous return catheter as defined in claim 7 in which the distal end of said body has a collar formed thereon to which the distal ends of said ribs are attached, and said tip is telescoped on and secured to said collar.

9. A single stage venous return catheter as defined in claim 2 in combination with an obturator which comprises:

(a) a hollow obturator tube to insert into said tubular connector of said catheter, and (b) an obturator head on the distal end of said tube comprising a hollow tip end to enter said rounded tip to provide a passage from the open distal end of said tip to the interior of said tube, axial ribs spaced circumferentially on said head at the proximal end of said tip end to enter and block the distal ends of said long slots, and a cylindrical portion proximally of said ribs to occlude said short slots and the proximal ends of said long slots, (c) whereby when said obturator is inserted into said main hollow cage body and said catheter is inserted into a heart vessel, flow of blood from said vessel can only enter the obturator tube.

* * * * *